(12) United States Patent
Klontz (10) Patent No.: US 12,396,633 B2
(45) Date of Patent: Aug. 26, 2025

(54) MULTI-CAMERA IMAGING SYSTEM

(71) Applicant: NVSurgical, LLC, Newton Center, MA (US)

(72) Inventor: Bryce C. Klontz, Boston, MA (US)

(73) Assignee: New View Medical, Inc., Newton Center, MA (US)

( * ) Notice: Subject to any disclaimer, the term of this patent is extended or adjusted under 35 U.S.C. 154(b) by 103 days.

(21) Appl. No.: 18/252,958

(22) PCT Filed: Nov. 9, 2021

(86) PCT No.: PCT/US2021/058662
§ 371 (c)(1),
(2) Date: May 15, 2023

(87) PCT Pub. No.: WO2022/103770
PCT Pub. Date: May 19, 2022

(65) Prior Publication Data
US 2024/0099572 A1    Mar. 28, 2024

Related U.S. Application Data

(60) Provisional application No. 63/112,398, filed on Nov. 11, 2020.

(51) Int. Cl.
*A61B 1/313* (2006.01)
*A61B 1/00* (2006.01)
(Continued)

(52) U.S. Cl.
CPC ........ *A61B 1/3132* (2013.01); *A61B 1/00009* (2013.01); *A61B 1/0005* (2013.01);
(Continued)

(58) Field of Classification Search
CPC . A61B 1/3132; A61B 1/00009; A61B 1/0005; A61B 1/045; A61B 2034/2048;
(Continued)

(56) References Cited

U.S. PATENT DOCUMENTS 5,453,094 A    9/1995  Metcalf et al.
5,554,097 A    9/1996  Guy
(Continued)

FOREIGN PATENT DOCUMENTS

CN    114404056    4/2022
EP     2415390    12/2012
(Continued)

OTHER PUBLICATIONS

International Search Report and Written Opinion; International Application No. PCT/US2021/058662; Feb. 23, 2022.
(Continued)

*Primary Examiner* — Michael E Teitelbaum
(74) *Attorney, Agent, or Firm* — Neil D. Gershon (57) ABSTRACT

Systems and methods are disclosed that combine image streams from two separate imaging units into a unified, augmented image. The systems and methods can combine the image streams based on relative spatial information of the imaging units. The spatial information can include distance, angle, and rotation of the imaging units relative to one another. In some implementations, the combined image stream can be a three-dimensional stereoscopic view.

19 Claims, 6 Drawing Sheets

(51) Int. Cl.
*A61B 1/045* (2006.01)
*G06T 5/50* (2006.01)
*H04N 5/265* (2006.01)
*H04N 23/50* (2023.01)
*H04N 23/51* (2023.01)

(52) U.S. Cl.
CPC .............. *A61B 1/045* (2013.01); *G06T 5/50* (2013.01); *H04N 5/265* (2013.01); *H04N 23/51* (2023.01); *H04N 23/555* (2023.01); *G06T 2207/10028* (2013.01); *G06T 2207/10068* (2013.01); *G06T 2207/20212* (2013.01)

(58) Field of Classification Search
CPC ........ A61B 2090/364; A61B 2090/367; A61B 2090/371; A61B 1/000095; A61B 1/0008; A61B 1/00097; A61B 1/018; A61B 1/00016; A61B 1/05; A61B 1/313; A61B 90/361; G06T 5/50; G06T 2207/10028; G06T 2207/10068; G06T 2207/20212; H04N 5/265; H04N 23/51; H04N 23/555
See application file for complete search history.

(56) References Cited

U.S. PATENT DOCUMENTS

| | | | |
|---|---|---|---|
| 6,006,126 | A | 12/1999 | Cosman |
| 6,419,626 | B1 | 7/2002 | Yoon |
| 6,984,205 | B2 | 1/2006 | Gazdzinski |
| 8,834,358 | B2 | 9/2014 | McKinley et al. |
| 10,264,978 | B2* | 4/2019 | Herzlinger ........... A61B 5/0084 |
| 10,568,658 | B2 | 2/2020 | Kahle et al. |
| 11,317,029 | B2 | 4/2022 | Blanquart et al. |
| 11,439,429 | B2 | 9/2022 | Zalewski |
| 2001/0039421 | A1 | 11/2001 | Heilbrun et al. |
| 2007/0112247 | A1 | 5/2007 | Hirata |
| 2009/0012530 | A1 | 1/2009 | Fowler |
| 2009/0219282 | A1* | 9/2009 | Kim ....................... H04N 19/50 375/E7.026 |
| 2012/0053406 | A1 | 3/2012 | Conlon et al. |
| 2014/0036051 | A1 | 2/2014 | Saito et al. |
| 2014/0052004 | A1 | 2/2014 | D'Alfonso et al. |
| 2014/0107417 | A1 | 4/2014 | McKinley |
| 2014/0171787 | A1 | 6/2014 | Garbey et al. |
| 2015/0216396 | A1 | 8/2015 | Banik et al. |
| 2016/0174828 | A1 | 6/2016 | Drach et al. |
| 2016/0192827 | A1 | 7/2016 | von Grunberg et al. |
| 2017/0079740 | A1 | 3/2017 | Hufnagel et al. |
| 2017/0231471 | A1 | 8/2017 | Nishio et al. |
| 2018/0055372 | A1 | 3/2018 | Watanabe et al. |
| 2019/0068846 | A1* | 2/2019 | Jung ..................... H04N 23/57 |
| 2019/0090959 | A1 | 3/2019 | Haider et al. |
| 2019/0110663 | A1 | 4/2019 | Nishio |
| 2019/0200848 | A1 | 7/2019 | McDowall et al. |
| 2019/0216325 | A1 | 7/2019 | Ouyang |
| 2019/0297238 | A1* | 9/2019 | Klosterman .............. G06T 7/37 |
| 2019/0328217 | A1 | 10/2019 | Moreau et al. |
| 2020/0222146 | A1 | 7/2020 | Komp |
| 2021/0236087 | A1 | 8/2021 | Dykes et al. |
| 2021/0290317 | A1* | 9/2021 | Sen ........................ A61B 34/20 |
| 2022/0070428 | A1 | 3/2022 | Komp et al. |
| 2022/0079442 | A1 | 3/2022 | Piron et al. |
| 2022/0096197 | A1 | 3/2022 | Song et al. |
| 2022/0122304 | A1 | 4/2022 | Muhsin et al. |
| 2022/0226047 | A1 | 7/2022 | Nekhendzy et al. |
| 2022/0280238 | A1 | 9/2022 | Fuerst et al. |
| 2022/0287556 | A1 | 9/2022 | Sikri |
| 2022/0296090 | A1 | 9/2022 | Ouyang et al. |
| 2022/0354603 | A1 | 11/2022 | Hasser et al. |
| 2023/0066803 | A1 | 3/2023 | Kayser et al. |
| 2023/0123739 | A1 | 4/2023 | Mino et al. |
| 2023/0414089 | A1* | 12/2023 | John ....................... A61B 1/05 |
| 2024/0041299 | A1 | 2/2024 | Kehat et al. |
| 2024/0071022 | A1 | 2/2024 | Graveley et al. |

FOREIGN PATENT DOCUMENTS

EP          3508814 A1     7/2019
WO     WO 2022/103770     5/2022

OTHER PUBLICATIONS

European Search Report EP 20 87 9524 mailing date: Oct. 17, 2023.
International Search Report PCT/US2024/018790 mailing date: Jul. 25, 2024.
European International Search Report and Written Opinion; European Application No. EP 21892685; dated Jul. 11, 2024.
International Search Report and Written Opinion; International Application No. PCT/US2024/018782; dated Jun. 7, 2024.
International Search Report and Written Opinion; International Application No. PCT/US2024/018784; dated Jun. 24, 2024.
International Search Report and Written Opinion; International Application No. PCT/US2024/018786; dated Jun. 13, 2024.
International Search Report and Written Opinion; International Application No. PCT/US2024/018788; dated Jul. 26, 2024.
International Search Report and Written Opinion; International Application No. PCT/US2024/018789; dated Jun. 18, 2024.

* cited by examiner

MULTI-CAMERA IMAGING SYSTEM

CROSS-REFERENCE TO RELATED APPLICATION

This application claims priority to U.S. Provisional Patent Application No. 63/112,398, which was filed on Nov. 11, 2020, the entire contents of which are incorporated herein by reference.

BACKGROUND

Minimally invasive surgery involves making small incisions into a body of a patient to insert surgical tools. For example, a surgeon may perform a laparoscopic procedure using multiple cannulas inserted through individual incisions that accommodate various surgical tools including illumination devices and imaging devices. To accomplish the insertion, trocars are used to puncture the body cavity. A trocar system often includes an obturator and a cannula. An obturator is a guide placed inside a cannula with either a sharp tip (e.g., a pointed cutting blade) or blunt tip for creating an incision for the cannula. After the cannula is inserted, the obturator is removed, leaving the cannula in place for use in inserting the surgical tools. A surgical tool combining a cannula and an imaging device in a single unit is disclosed, for example. in U.S. Pat. No. 8,834,358, the disclosure of which is herein incorporated by reference in its entirety.

SUMMARY

In some implementations, the present disclosure provides an imaging system including a display device, an imaging controller, a first imaging unit, a second imaging unit, and a processor. The imaging controller can include a computer-readable data storage device storing program instructions that, when executed by the processor, control the system to perform operations including receiving a first image stream and spatial information from the first imaging unit. The operations also include receiving a second image stream from the second imaging unit. The operations can further include combining the first image stream and the second image stream based the spatial information.

Additionally, in some implementations, the present disclosure provides an endoscopic imaging unit including a housing, a controller, a body, a sensor housing, and antennas. The sensor housing can include an image sensor, a LiDAR device, and a light source. Also, the controller can include spatial sensors, a transmitter/receiver, and a processor. Further, the body and the sensor housing can be configured to be inserted into a body of a subject.

Further, in some implementations, the present disclosure provides method including, receiving a first image stream and first spatial information from a first imaging unit. The method can also include receiving a second image stream and second spatial information from a second imaging unit. The method can further include determining spatial relationships between the first imaging unit and the second imaging unit. Additionally, the method can include determining whether one or more of the spatial relationships exceed one or one or more thresholds. Further, the method can include generating a combined image stream using the first image stream and the second image stream, and using the first spatial information and the second spatial information.

DETAILED DESCRIPTION

The present disclosure relates generally to imaging systems and, more particularly, to endoscopic imaging systems. Systems and methods in accordance with aspects of the present disclosure combine image streams from two separate imaging units into a unified, augmented image. In some implementations, the imaging units are endoscopic devices.

Systems and methods in accordance with aspects of the present disclosure can combine image streams from separate imaging units based on relative spatial information of the imaging units. In implementations, the spatial information can include, for example, distance, angle, and rotation of the imaging units relative to one another. In some implementations, the combined image stream can be, for example, a three-dimensional ("3D") stereoscopic view. Also, in some implementations the combined image stream can have a wider field of view than individually provided by a single one of either imaging unit. Additionally, in some implementations the system can identify and characterize structures, such as tools or tissues, in the images, from combined image stream. Moreover, in some implementations the system can remove obstructions between the respective views of the imaging units from the combined image stream. Further, in some implementations, the systems and methods can also combine images from a secondary image source, such as a computed tomography ("CT") scanner, with the combined image stream of the imaging units.

Reference will now be made in detail to specific implementations illustrated in the accompanying drawings. In the following detailed description, numerous specific details are set forth to provide a thorough understanding of the disclosure. However, it will be apparent to one of ordinary skill in the art that implementations may be practiced without these specific details. In other instances, known methods, procedures, components, circuits, and networks have not been described in detail so as not to unnecessarily obscure aspects of the implementations.

Figure 1:
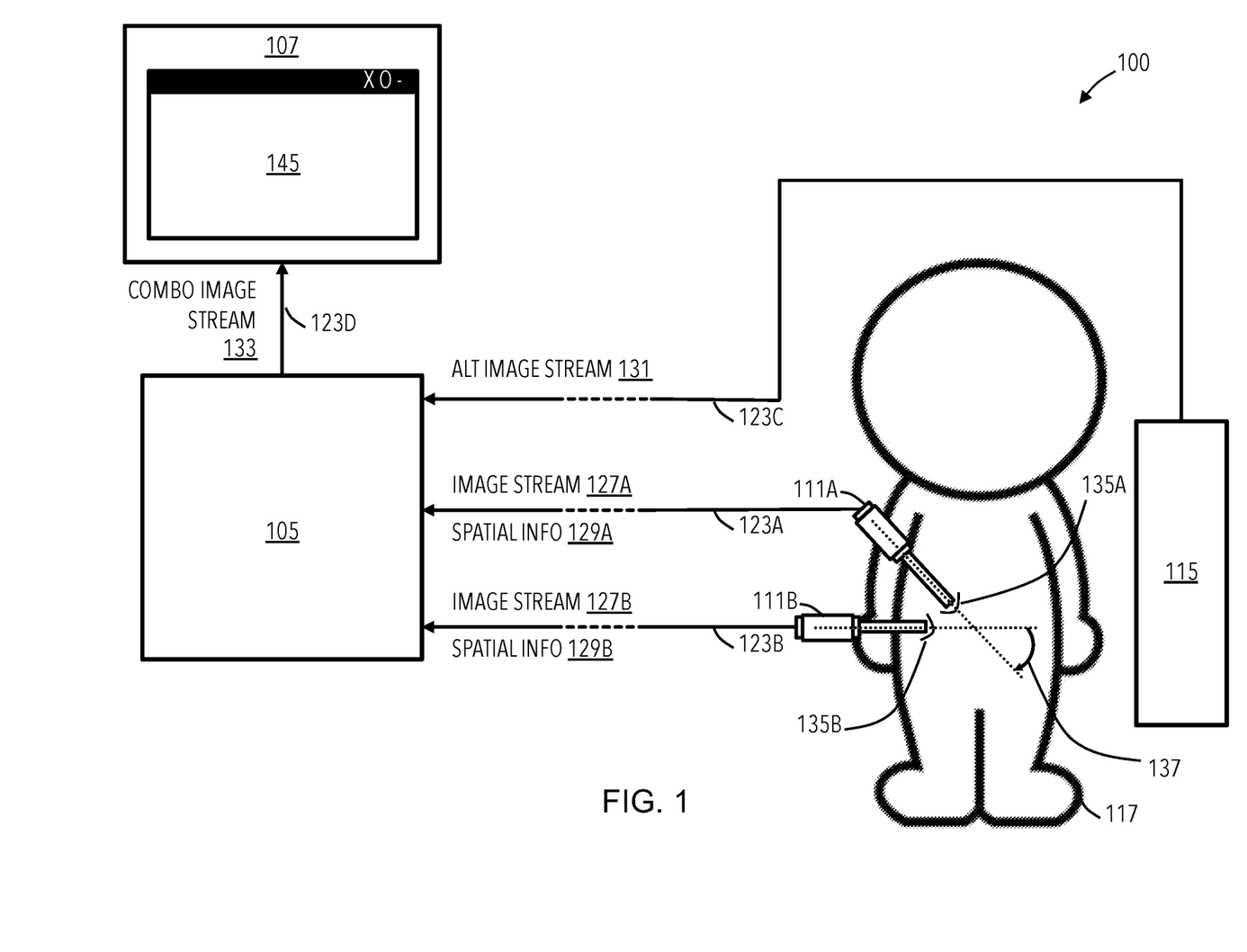
FIG. 1 shows a system block diagram illustrating an example of an environment for implementing systems and processes in accordance with aspects of the present disclosure.

FIG. 1 shows a block diagram illustrating an example of an environment 100 for implementing systems and methods in accordance with aspects of the present disclosure. In some implementations, the environment 100 can include an imaging controller 105, a display device 107, imaging units 111A, 111B, a secondary imaging system 115, and a subject 117. The imaging controller 105 can be a computing device connected to the display device 107, the imaging units 111A, 111B, and the secondary imaging system 115 through one or more wired or wireless communication channels 123A, 123B, 123C, 123D. The communication channels 123A, 123B, 123C may use various serial, parallel, video transmission protocols suitable for their respective signals such as image streams 127A, 127B, 131, and 133, and data signals, such as spatial information 129A, 129B.

The imaging controller 105 can include hardware, software, or a combination thereof for performing operations in accordance with the present disclosure. The operations can include receiving the respective image streams 127A, 127B and the spatial information 129A, 129B from the imaging units 111A, 111B. The operations can also include processing the spatial information 129A, 129B to determine relative positions, angles, and rotations of the imaging units 111A, 111B. In some implementations, the images streams 127A, 127B and the spatial information 129A, 129B can be substantially synchronous, real-time information captured by the imaging units 111A, 111B. In some implementations, determining the relative positions, angles, and rotations includes determining respective fields-of-view of the imaging units 111A, 111B. For example, the relative visual perspective can include a relative distance, angle and rotation of the imaging units' 111A, 111B fields-of-view.

The operations of the imaging controller 105 can also include combining the image streams 127A, 127B into the combined image stream 133 based on the spatial information 129A, 129B. In some implementations, combining the image streams 127A, 127B includes registering and stitching together the images in the fields-of-view of the imaging units 111A, 111B based on the spatial information 129A, 129B. The combined image stream 133 can provide an enhanced display 145 of the subject 117, who can be a surgical patient. For example, the imaging controller 105 can generate the combined image stream 133 to selectably enhance the field-of-view of one of the imaging units 111A, 111B based on the field-of-view of the other imaging unit 111A, 111B. In some implementations, the enhanced display 145 may be a stereoscopic 3D view from the perspective of one of the imaging units 111A, 111B.

Additionally, the operations of the imaging controller 105 can include identifying, characterizing, and removing structures included in the combination of the image streams 127A, 127B. In some implementations, using the spatial information 129A, 129B, the imaging controller 105 can identify and remove images of physical structures in the overlapping fields-of-view of the imaging unit 111A using the image streams 127A, 127B, and the spatial information 129A, 129B. For example, the obstruction can be a sensor housing (e.g., sensor housing 217) or it can be a portion of the subject's 117 bowels in the subject's 117 body cavity that blocks the field-of-view of the first imaging unit 111A or the second imaging unit 111B. The imaging controller 105 can determine the size and location of the obstruction and automatically process the image streams 127A, 127B to remove the obstruction from the combined images stream 133 and the enhanced display 145.

The display device 107 can be one or more devices that can display the enhanced display 145 for an operator of the imaging units 111A, 111B. As described above, the display device 107 can receive the combined image stream 133 and display the enhanced image 145, which can include an augmented combination of the respective image streams 127A, 127B from the imaging units 111A, 111B. The display device 107 can be a liquid crystal display (LCD) display, organic light emitting diode displays (OLED), cathode ray tube display, or other suitable display device. In some implementations, the display device 107 can be a stereoscopic head-mounted display, such as a virtual reality headset.

The imaging units 111A, 111B can be devices including various sensors that generate the image streams 127A, 127B and the spatial information 129A, 129B. In some implementations, the imaging units 111A, 111B are endoscopic devices configured to be inserted in the body of the subject 117, as previously described herein. For example, the imaging units 111A, 111B can be laparoscopic instruments used to visualize a body cavity of the subject 117 and record images inside the body cavity. As illustrated in FIG. 1, the imaging units 111A, 111B can be inserted into the subject 117 at different locations 135A, 135B (e.g., ports) and positioned at an angle 137 with respect to each other so as to provide overlapping fields-of-view inside a body cavity of the subject 117. The imaging units 111A, 111B can also be rotated relative to one another around their long axes. For example, the imaging controller 105 can provide feedback to a surgeon via the display device 107 to translate and rotate the imaging units 111A, 111B in the subject 117 such that the imaging units 111A, 111B have overlapping field-of-views within sufficient distance, angle, and orientation thresholds for stitching the image streams 127A, 127B into the combined image stream 133.

The secondary imaging system 115 can be an apparatus that provides one or more alternate image streams 131 of the subject 117. In some implementations, the alternate images 131 comprise a substantially real-time image stream. The secondary imaging system 115 can be, for example, a CT scanning system, an X-ray imaging system, an ultrasound system, a fluorescence imaging system (e.g., indocyanine green fluorescence), or other multi-spectral wavelength system. In some implementations, the imaging controller 105 can process the alternate image stream 131 to further combine them with the combination of image streams 127A, 127B. For example, the imaging controller 105 can generate the combination image stream 133 by overlaying a synchronized image stream with a 3D stereoscopic images generated using the image streams 127A, 127B.

Figure 2:
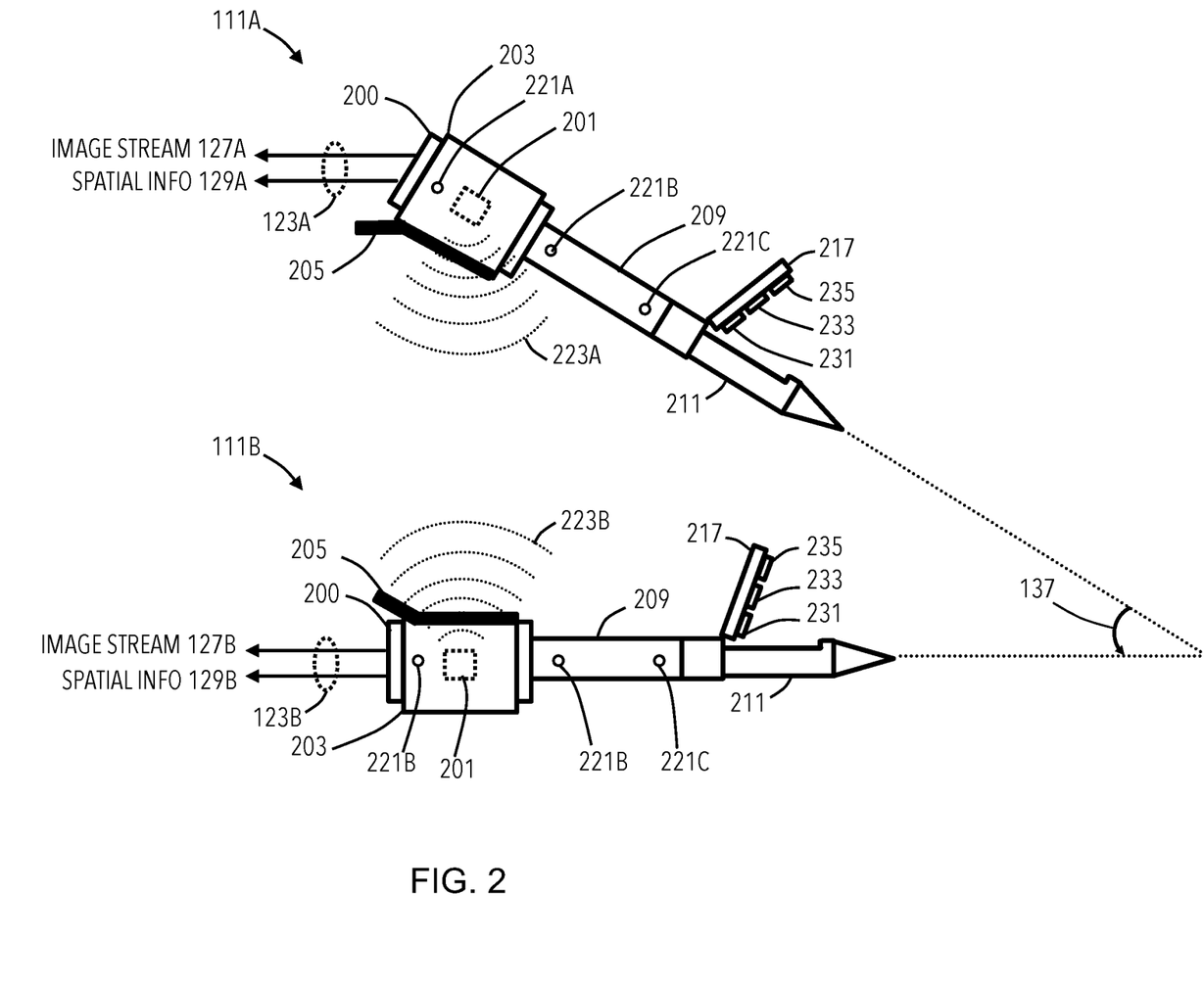
FIG. 2 shows a system block diagram illustrating examples of imaging units in accordance with aspects of the present disclosure.

FIG. 2 shows a system diagram illustrating examples of imaging units 111A, 111B in accordance with aspects of the present disclosure. The imaging units 111A, 111B can be the same or similar to those discussed above. In some implementations, the imaging units 111A, 111B can include a housing 200, a device controller 201, a body 203, an actuator handle 205, a cannula 209, an obturator 211, a sensor housing 217, and antennas 221A, 221B, 221C. The cannula 209, the obturator 211, and the sensor housing 217 of the individual imaging units 111A, 111B can be inserted into the body of a subject (e.g., subject 117) and positioned at an angle 137 with respect to each other so as to provide overlapping fields-of-view from the sensor housing 217.

The device controller 201 can be one or more devices that process signals and data to generate respective image streams 127A, 127B and spatial information 129A, 129B of the imaging units 111A, 111B. In some implementations, the device controller 201 can determine the spatial information 129A, 129B by processing data from spatial sensors (e.g., accelerometers) to determine the relative position, angle, and rotation of the imaging units 111A, 111B. Also, in some implementations, the device controller 201 can also determine the spatial information 129A, 129B by processing range information received from sensors (e.g., image sensor 231 and LiDAR device 233) in the sensor housing 217. Additionally, in some implementations, the device controller 201 can process the spatial information 129A, 129B by processing signals received via the antennas 221A, 221B, 221C to determine relative distances of the imaging units 111A, 111B. It is understood that, in some implementations, only one of the imaging units 111A, 111B provides spatial information 129.

The cannula 209 may be formed of a variety of cross-sectional shapes. For example, the cannulas 209 can have a generally round or cylindrical, ellipsoidal, triangular, square, rectangular, and D-shaped (in which one side is flat). In some implementations, the cannula 209 includes an internal lumen 202 that retains the obturator 211. The obturator 211 can be retractable and/or removable from the cannula 209. In some implementations, the obturator 211 is made of solid, non-transparent material. In another implementation, all or parts of the obturator 211 are made of optically transparent or transmissive material such that the obturator 211 does not obstruct the view through the camera (discussed below).

The sensor housing 217 can be integral with the cannula 209 or it may be formed as a separate component that is coupled to the cannula 209. In either case, the sensor housing 217 can disposed on or coupled to the cannula 209 at a position proximal to the distal end of the cannula 209. In some implementations, the sensor housing 217 can be actuated by the actuator handle 205 to open, for example, after inserted into the subject's 117 body cavity. The sensor housing 217 can reside along tube 110 in the distal direction such that it is positioned within the body cavity of a subject (e.g., subject 117). At the same time, sensor housing 217 can be positioned proximal to distal end such that it does not interfere with the insertion of the distal end of the cannula 209 as it is inserted into a subject (e.g., subject 117). In addition, the sensor housing 217 can positioned proximally from distal end to protect the electronic components therein as distal end creates is inserted into the subject.

In some implementations, the sensor housing 217 can include one or more image sensors 231, a LiDAR device 233, and a light source 235. The light source 235 can be dimmable light-emitting device, such as a LED, a halogen bulb, an incandescent bulb, or other suitable light emitter. The image sensors 231 can be devices configured to detect light reflected from the light source 235 and output an image signal. The image sensor 231 can be, for example, a charged coupled device ("CCD") or other suitable imaging sensor. In some implementations, the image sensor 231 includes at least two lenses providing stereo imaging. In some implementations, the image sensor 231 can be an omnidirectional camera.

The LiDAR device 233 can include one or more devices that illuminate a region with light beams, such as lasers, and determine distance by measuring reflected light with a photosensor. The distance can be determined based a time difference between the transmission of the beam and detection of backscattered light. For example, using the LiDAR device 233, the device controller 201 can determine spatial information 129 by sensing the relative distance and rotation of the cannulas 209 or the sensor housing 217 inside a body cavity.

Additionally, the antennas 221A, 221B, 221C can be disposed along the long axis of the imaging units 111A, 111B. In some implementations, the antennas 221A, 221B, 221C can be placed in a substantially straight line on one or more sides of the imaging units 111A, 111B. For example, two or more lines of the antennas 221A, 221B, 221C can be located on opposing sides of the housing 203 and the cannula 209. Although FIG. 2 shows a single line of the antennas 221A, 221B, 221C on one side of the imaging units 111A, 111B, it is understood that the additional lines of the antennas 221A, 221B, 221C can be placed in opposing halves, thirds, or quadrants of the imaging units 111A, 111B.

As illustrated in FIG. 2, the device controllers 201 can transmit a ranging signal 223. In some implementations, the location signals are ultra-wideband ("UWB") radio signal usable to determine a distance between the imaging units 111A, 111B less than or equal to 1 centimeter based on signal phase and amplitude of the radio signals, as described in IEEE 802.15.4Z. The device controller 201 can determine the distances between the imaging units 111A, 111B based on the different arrival times of the ranging signals 223A and 223B at their respective antennas 221A, 221B, 221C. For example, referring to FIG. 3, the ranging signal 223A emitted by imaging unit 111A can be received by imaging unit 111B at antenna 221C and an amount of time (T) after arriving at antenna 221B. By making a comparison of the varying times of arrival of the ranging signal 223A at two or more of the antennas 221A, 221B, 221C, the device controller 201 of imaging unit 111B can determine its distance and angle from imaging unit 111A. It is understood that the transmitters can be placed at various suitable locations within the imaging units 111A, 111B. For example, in some implementation, the transmitters can be located in the cannulas 209 or in the sensor housings 217.

Figure 3:
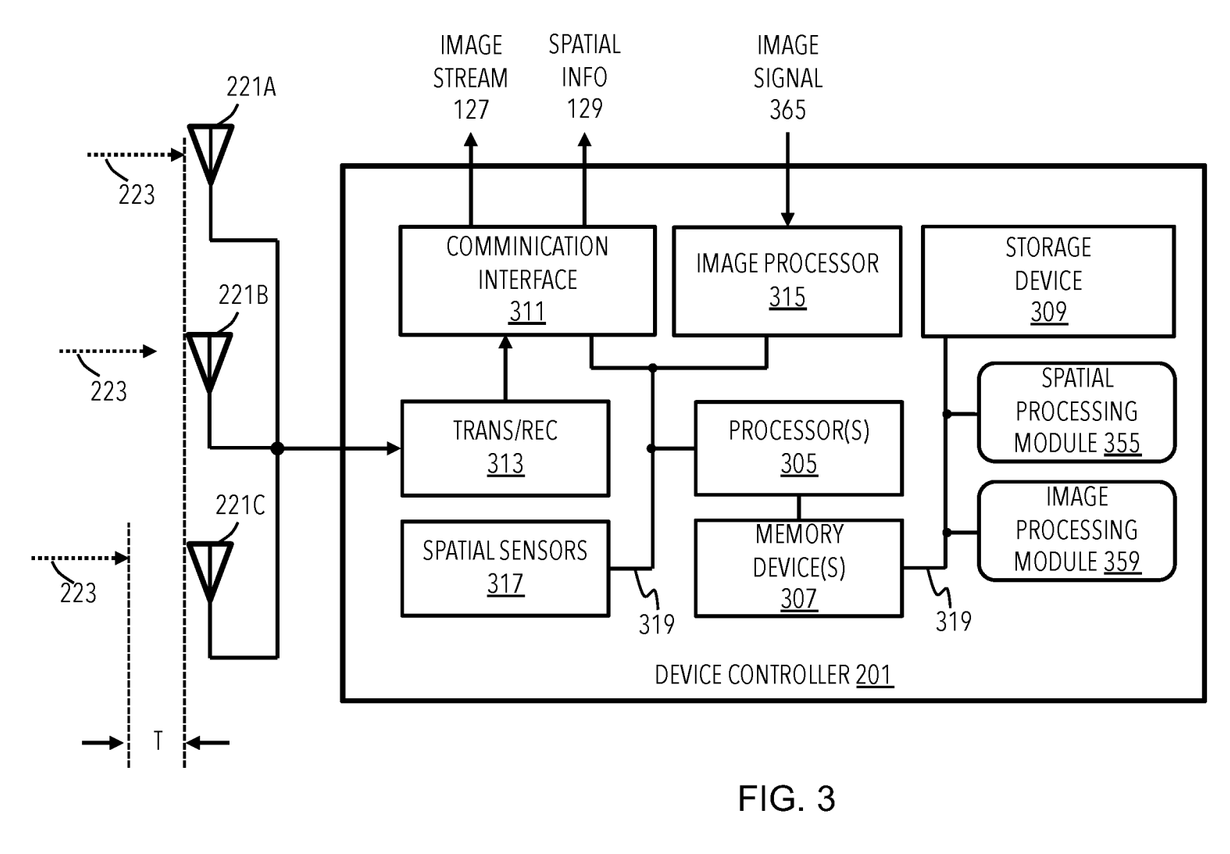
FIG. 3 shows a block diagram illustrating an example of a device controller in accordance with aspects of the present disclosure.

FIG. 3 shows a functional block diagram illustrating an example of a device controller 201 in accordance with aspects of the present disclosure. The device controller 201 can be the same or similar to that described above. In some implementations, the device controller 201 can include a processor 305, a memory device 307, a storage device 309, a communication interface 311, a transmitter/receiver 313, an image processor 315, spatial sensors 317, and a data bus 319.

In some implementations, the processor 305 can include one or more microprocessors, microchips, or application-specific integrated circuits. The memory device 307 can include one or more types of random-access memory (RAM), read-only memory (ROM) and cache memory employed during execution of program instructions. The processor 305 can use the data buses 319 to communicate with the memory device 307, the storage device 309, the communication interface 311, the image processor 315, and the spatial sensors 317. The storage device 309 can comprise a computer-readable, non-volatile hardware storage device that stores information and program instructions. For example, the storage device 309 can be one or more, flash drives and/or hard disk drives. The transmitter/receiver 313 can be one or more devices that encodes/decodes data into wireless signals, such as the ranging signal 223.

The processor 305 executes program instructions (e.g., an operating system and/or application programs), which can be stored in the memory device 307 and/or the storage device 309. The processor 305 can also execute program instructions of a spatial processing module 355 and an image processing module 359. The spatial processing module 335 can include program instructions that determine the spatial information 129 by combining spatial data provided from the transmitter/receiver 313 and the spatial sensors 317. The image processing module 359 can include program instructions that, using the image signal 127 from an imaging sensor (e.g., image sensor 231), register and stitch the images to generate the image stream 127. The image processor 315 can be a device configured to receive an image signal 365 from an image sensor (e.g., image sensor 231) and condition images included in the image signal 365. In accordance with aspects of the present disclosure, conditioning the image signal 365 can include normalizing the size, exposure, and brightness of the images. Also, conditioning the image signal 365 can include removing visual artifacts and stabilizing the images to reduce blurring due to motion. Additionally, the image processing module 359 can be identify and characterize structures in the images.

In some implementations, the spatial sensors 317 can include one or more of, piezoelectric sensors, mechanical sensors (e.g., a microelectronic mechanical system ("MEMS"), or other suitable sensors for detecting the location, velocity, acceleration, and rotation of the imaging units (e.g., imaging units 111A, 111B).

It is noted that the device controller 201 is only representative of various possible equivalent-computing devices that can perform the processes and functions described herein. To this extent, in some implementations, the functionality provided by the device controller 201 can be any combination of general and/or specific purpose hardware and/or program instructions. In each implementation, the program instructions and hardware can be created using standard programming and engineering techniques.

Figure 4:
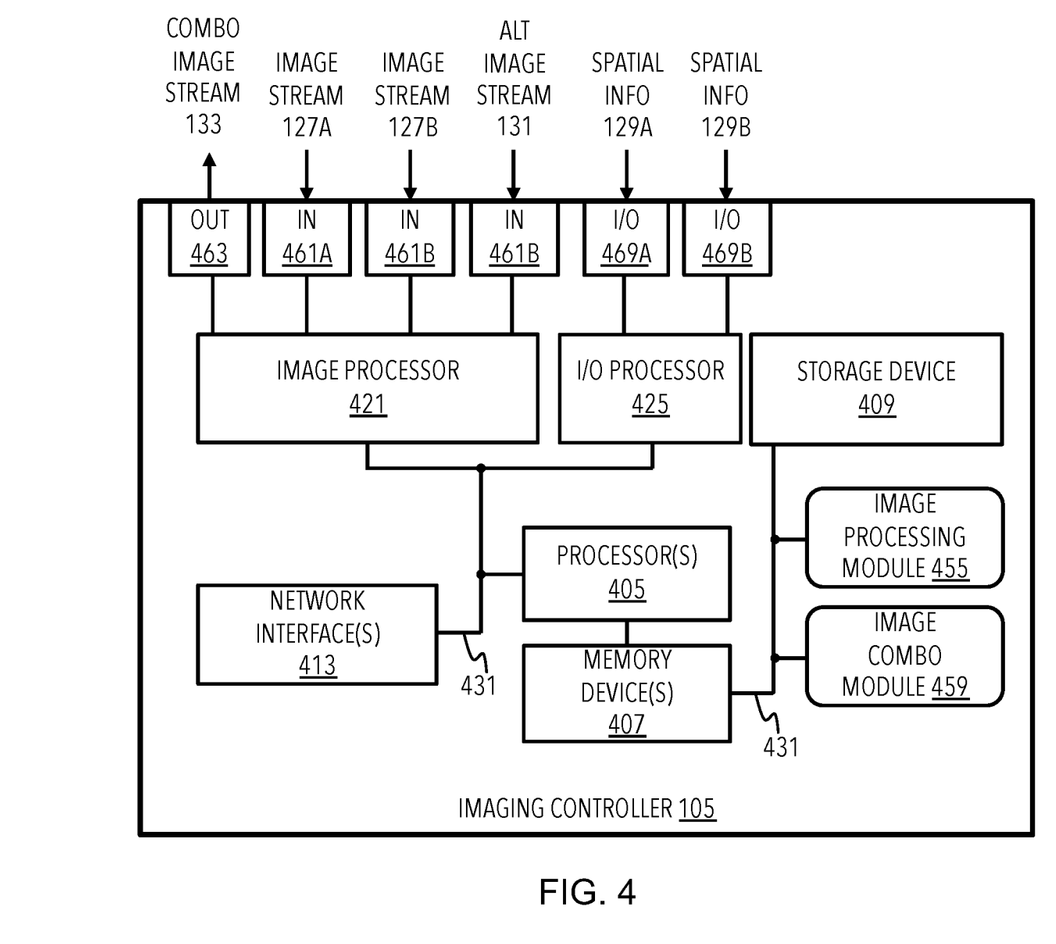
FIG. 4 shows a block diagram illustrating an example of an imaging controller for a system in accordance with aspects of the present disclosure.

FIG. 4 shows a functional block diagram illustrating an imaging controller 105 in accordance with aspects of the present disclosure. The imaging controller 105 can be the same or similar to that previously described herein. The imaging controller 105 can include a processor 405, a memory device 407, a storage device 409, a network interface 413, an image processor 421, an I/O processor 425, and a data bus 431. Also, the imaging controller 105 can include image input connections 461A, 461B, 461C, image output connection 463 that receive and transmit image signals from the image processor 421. Further, the imaging controller 105 can include input/output connections 469A, 439B that receive/transmit data signals from I/O processor 425.

In implementations, the imaging controller 105 can include one or more microprocessors, microchips, or application-specific integrated circuits. The memory device 407 can include one or more types of random-access memory (RAM), read-only memory (ROM) and cache memory employed during execution of program instructions. Additionally, the imaging controller 105 can include one or more data buses 431 by which it communicates with the memory device 407, the storage device 409, the network interface 413, the image processor 421, and the I/O processor 425. The storage device 409 can comprise a computer-readable, non-volatile hardware storage device that stores information and program instructions. For example, the storage device 409 can be one or more, flash drives and/or hard disk drives.

The I/O processor 425 can be connected the processor 405 can include any device that enables an individual to interact with the processor 405 (e.g., a user interface) and/or any device that enables the processor 405 to communicate with one or more other computing devices using any type of communications link. The I/O processor 425 can generate and receive, for example, digital and analog inputs/outputs according to various data transmission protocols.

The processor 405 executes program instructions (e.g., an operating system and/or application programs), which can be stored in the memory device 407 and/or the storage device 409. The processor 405 can also execute program instructions of an image processing module 455 and an image combination module 459. The image processing module 455 can be configured to stabilize the images to reduce the blurring, compensate for differences in tilt and rotation, remove reflections and other visual artifacts from the images, and normalize the images. Additionally, the image processing module 455 can be configured to identify and characterize structures, such as tools or tissues, in the images. Further, the imaging processing module 455 can be configured to determine obstructions in the overlapping fields of view and process the images streams 127A, 127B to remove the obstructions.

The image combination module 459 can be configured to analyze images received in an image streams 127A, 127B from the imaging units and combine them into a single, combined image stream 133 based on the spatial information. In some implementations, the image combination module 459 generates the combination image stream 133 by registering and stitching together the image streams 127A, 127B based on the respective fields-of-view of the imaging units. In some implementations, either of the imaging units can be selected by an operator as a primary imaging unit (e.g., imaging unit 111A), and the image combination module 459 can generate the combination image stream 133 by using the image stream 127B of the secondary imaging unit to augment the image stream 127A. The combination image stream 133 can provide an improved field of view than the field of view of the image stream 127A. The combination image stream 133 can also provide a 3D view from the perspective of the primary imaging unit. In some implementations, the combination image stream 133 lacks the obstructions removed by the image processing module 455. In some implementations, the combination image stream 133 also includes images provided by a secondary imaging system (e.g., secondary imaging system 115).

It is noted that the imaging controller 105 is only representative of various possible equivalent-computing devices that can perform the processes and functions described herein. To this extent, in some implementations, the functionality provided by the imaging controller 105 can be any combination of general and/or specific purpose hardware and/or program instructions. In each implementation, the program instructions and hardware can be created using standard programming and engineering techniques.

Figure 5A:
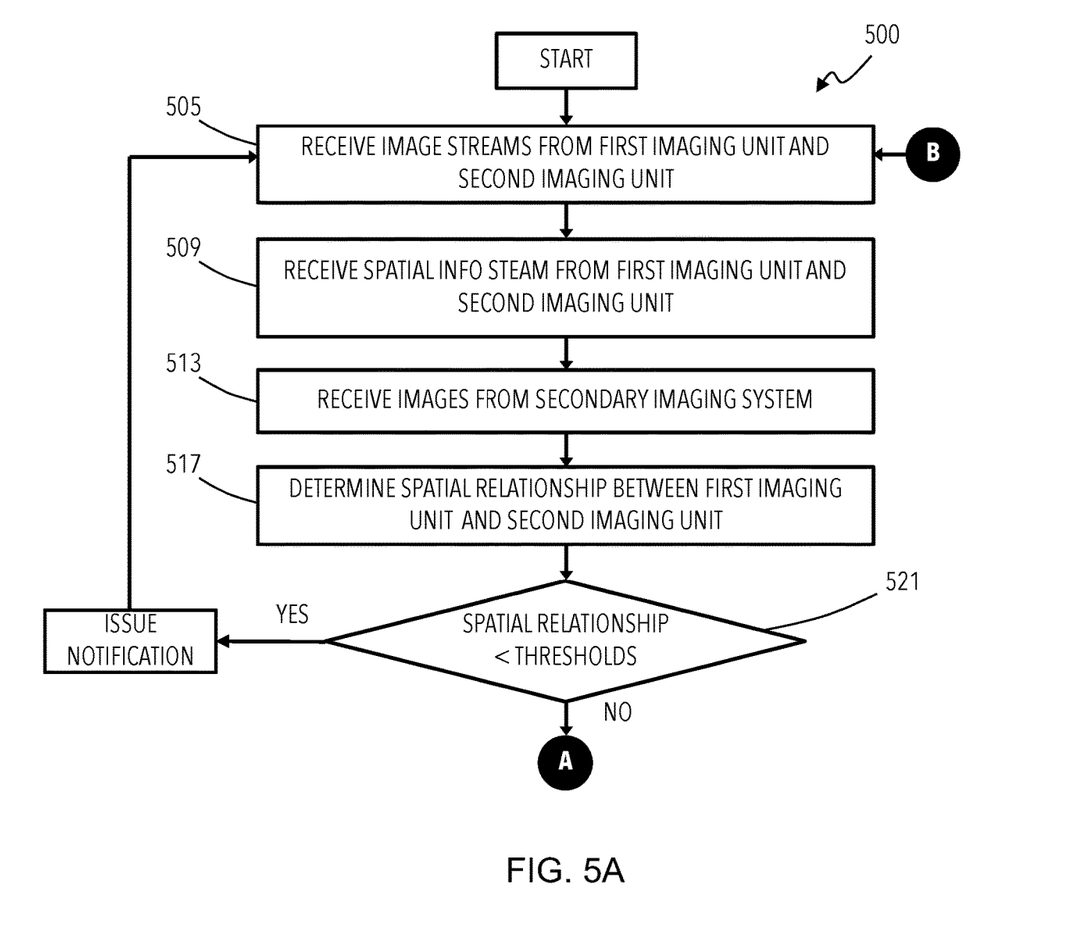
FIGS. 5A and 5B show a flow block diagram illustrating an example of a method performed by a system in accordance with aspects of the present disclosure.
Figure 5B:
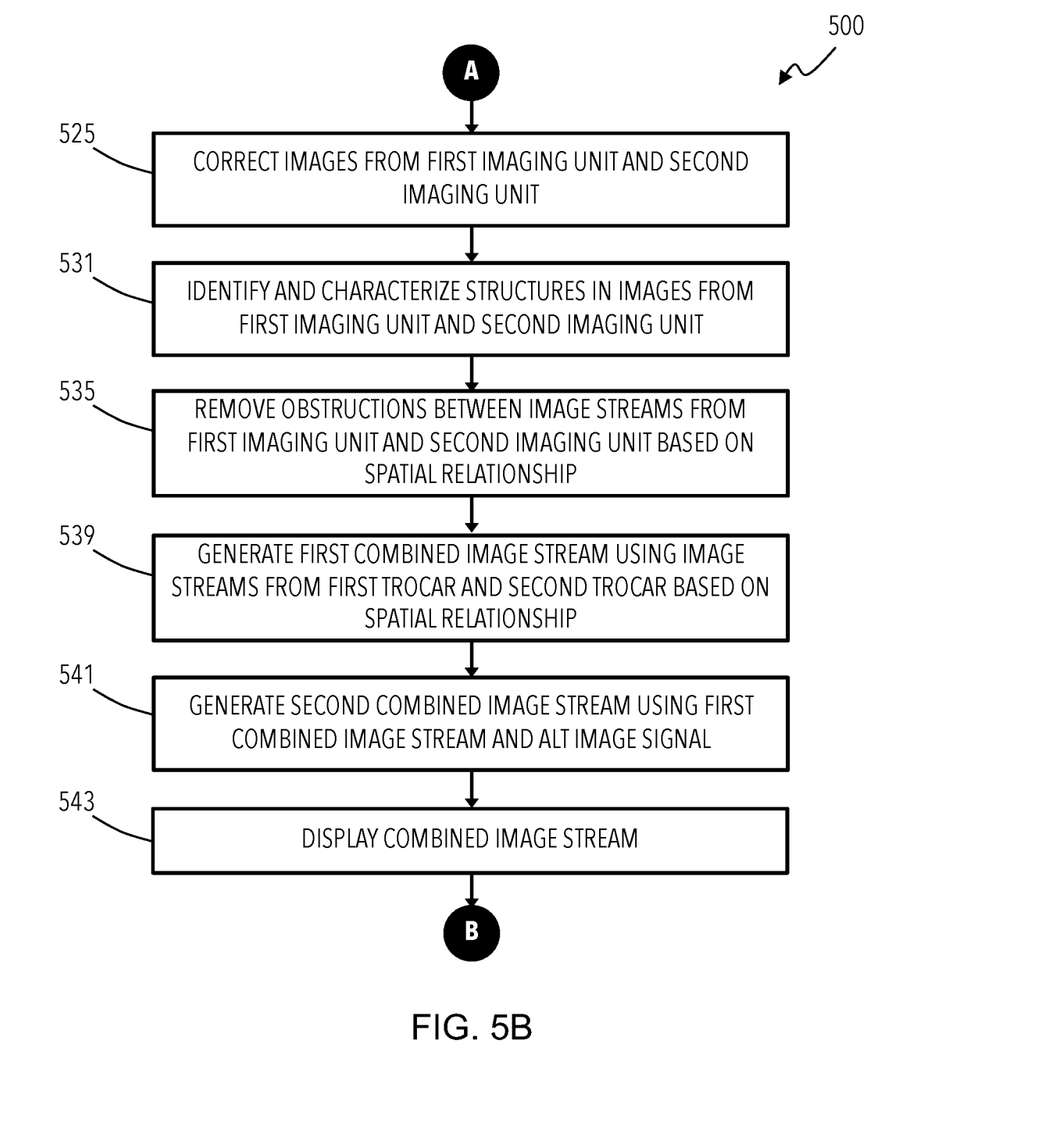

The flow diagram in FIGS. 5A and 5B illustrates an example of the functionality and operation of possible implementations of systems, methods, and computer program products according to various implementations consistent with the present disclosure. Each block in the flow diagram of FIGS. 5A and 5B can represent a module, segment, or portion of program instructions, which includes one or more computer executable instructions for implementing the illustrated functions and operations. In some alternative implementations, the functions and/or operations illustrated in a particular block of the flow diagram can occur out of the order shown in FIGS. 5A and 5B. For example, two blocks shown in succession can be executed substantially concurrently, or the blocks can sometimes be executed in the reverse order, depending upon the functionality involved. It will also be noted that each block of the flow diagram and combinations of blocks in the block can be implemented by special purpose hardware-based systems that perform the specified functions or acts, or combinations of special purpose hardware and computer instructions.

FIGS. 5A and 5B show a flow block diagram illustrating an example of a method 500 for generating a combined image stream from individual image streams generated by multiple different imaging units. Referring to FIG. 5A, at block 505 the system receives image streams (e.g., image streams 127A, 127B) from a first imaging unit (e.g., imaging unit 111A) and a second imaging unit (imaging unit 111B). For example, the imaging units can be included in a cannula placed within a subject's (e.g., subject 117) abdomen by a surgeon.

At block 509, the system can receive spatial information (e.g., spatial information 129A, 129B) from the first imaging unit and the second imaging unit. The spatial information can be time-synchronized with the respective image streams received at block 505. In some implementations, the spatial information is received substantially simultaneously and substantially synchronously with the image streams received at block 505. The spatial information can include distances, angles, and rotations of the imaging units with respect to one another or with respect to a reference position (e.g., top dead center).

At block 513, the system can receive images (e.g., alternate image stream 131) from a secondary imaging system (e.g., secondary imaging system 115), which can be a CT scanner, X-ray imager, an ultrasound system, or a fluorescence imaging system, for example. In some implementations, the images from the secondary imaging system can received substantially simultaneously and substantially synchronously with the respective image streams received at block 505 and the spatial information received at block 509.

At block 517, the system can determine spatial relationships between the first imaging unit and the second imaging unit. In some implementations, determining the spatial relationships includes determining overlapping fields-of-view-of the imaging units. Additionally, in some implementations, determining the spatial relationships includes determining a relative distance, angle, and orientation of the imaging units. For example, using the spatial information, the system can determine the relative distance, angle, and rotation of the sensor housings. Further, in some implementations, determining the spatial relationships between the first imaging unit and the second imaging unit can include analyzing respective images of the first imaging unit and the second imaging unit using computer vision techniques.

At block 521, the system determines whether the spatial relationship between determined at block 517 exceeds one or more predefined thresholds. For example, the system can determine whether an angle (e.g., angle 137) and rotation of first imaging unit relative to the second imaging unit exceeds respective maximum values (e.g. 45 degrees). If the system determines that one or more of the spatial relationships exceeds their thresholds at block 521 (e.g., block 521 is "Yes"), then at block 523 the system can issue a notification indicating to an operator to reposition the imaging units to adjust their alignment and the method can iteratively return to block 505. In some implementations, the notification can be displayed (e.g., via screen 145 using display 107) to the operator along with guidance for correcting the issue. The guidance can include, for example, positive and negative feedback indicating positional, angular, and rotational changes to bring spatial relationship within the maximum values.

On the other hand, if the system determines at block 521 that the distance, angle, and orientation is less than or equal to a respective one of the thresholds, then as indicated by off-page connector "A," at block 525 of FIG. 5B, the system (e.g., executing image processing module 455) can process the image streams received at block 505 to correct the images received from the first and second imaging units. Correcting the images can include stabilizing the images to reduce the blurring of the images due to of vibrations and other movements of the imaging units, individually and with respect to one another. Correcting the images can also include correcting the spatial relationships of the images to compensate for differences in tilt and rotation of the imaging units. Further, correcting the images can include removing specular reflections and other visual artifacts from the images. Moreover, correcting the images can include normalizing the images for exposure, color, contrast, and the like.

At block 531, the system can identify and characterize structures in images from first imaging unit and second imaging unit. In some implementations, the system can analyze the images of the individual or the combined image streams to identify regions and boundaries of particular structures. For example, the system can extract features to obtain a collection of locations and data, and interpolated it using pattern recognition algorithms for example, to determine the shapes and relative spatial positions of structures. At block 535, the system can remove obstructions between the first imaging unit and the second imaging unit based on the spatial relationships determined at block 517 and the structures identified at block 531. For example, the system remove the sensor housing or tissues from images comprising the combined image stream.

At block 539, the system can generate a first combined image stream (e.g., combination image stream 133) using the image streams received at block 505 or modified at blocks 525 and 535 using the spatial information received at block 509 and the spatial relationships determined at block 517. For example, as described above, the system can register and stitch together images in the image streams to provide an augmented field-of-view. At block 541, the system can generate the combined image stream by also combining the image stream generated at block 539 with the images received in an image stream from the secondary source at block 513. At block 543, the system can generate a display (e.g., an images 145) using the image streams combined at blocks 527 or 531 on a display device (e.g., display device 107). The method can then iteratively return to block 505 of FIG. 5A, as indicated by off-page connector "B."

The present disclosure is not to be limited in terms of the particular implementations described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is also to be understood that the terminology used herein is for the purpose of describing examples of implementations, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to some implementations containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

What is claimed is:

1. An imaging system comprising:
   a display device;
   an imaging controller;
   a first imaging unit configured to be inserted into a body of a subject;
   a second imaging unit configured to be inserted into a the body of the subject; and
   a processor,
   wherein the imaging controller includes a computer-readable data storage device storing program instructions that, when executed by the processor, control the system to:
     receive a first image stream and spatial information from the first imaging unit;
     receive a second image stream from the second imaging unit;
     combine the first image stream and the second image stream based on the spatial information;
     determine spatial relationships between the first imaging unit and the second imaging unit;
     determine whether the spatial relationships exceed or are below one or more thresholds; and
     in response to determining whether the spatial relationships exceed or are below the one or more thresholds, provide a notification to an operator or process the first and second image streams to correct images received.

2. The imaging system of claim 1, wherein the spatial information comprises distance, rotation, and angle information of the first imaging unit relative to the second imaging unit.

3. The imaging system of claim 1, wherein the first imaging unit and the second imaging units individually comprise a cannula and a sensor housing.

4. The imaging system of claim 3, wherein:
   the sensor housing of the first imaging unit comprises a first imaging sensor configured to generate the first image stream; and
   the sensor housing of the second imaging unit comprises a second imaging sensor configure to generate the second image stream.

5. The imaging system of claim 4, wherein:
   the sensor housing of the first imaging unit comprises a first LiDAR device configured to generate the spatial information.

6. The imaging system of claim 5, wherein the spatial information further comprises a distance and rotation of the first imaging unit relative to the second imaging unit.

7. The imaging system of claim 1, wherein combining the first image stream and the second image stream comprises registering and stitching images of the first image stream with images of the second image stream.

8. The imaging system of claim 7, wherein the images of the first image stream, the images of the second image stream, and the spatial information are time-synchronized.

9. The imaging system of claim 1, wherein program instructions further control the system to:
   display, using the combination of the first image stream and the second image stream, an augmented version of the second image stream.

10. The endoscopic imaging unit of claim 2, wherein the first imaging unit comprises:
    a plurality of antennas configured to receive a ranging signal from the second imaging unit; and
    the spatial information is determined by determining the distances from the second imaging unit based on a difference of arrival times of the ranging signal at the plurality of antennas.

11. The endoscopic imaging unit of claim 3, wherein the cannula is configured to receive an obturator.

12. The imaging system of claim 3, wherein the sensor housing of the first imaging unit comprises one or more image sensors, a LiDAR device, and a light source.

13. The imaging system of claim 10, wherein the plurality of antennas are placed in a substantially straight line on one or more sides of the first and second imaging units.

14. The imaging system of claim 1, wherein the imaging controller is configured to identify and remove images of physical structures in overlapping fields-of-view.

15. The imaging system of claim 14, wherein the controller is configured to remove the images of physical structures using the first and second image streams and the spatial information.

16. The imaging system of claim 1, wherein the imaging controller provides feedback to an operator via a display device to one or both of translate or rotate one or both of the first and second imaging units to provide overlapping fields-of-view within thresholds.

17. The imaging system of claim 1, wherein the notification is provided in response to the determining that the spatial relationships exceed the one or more thresholds, and wherein the notification in particular comprises positive and negative feedback indicating positional, angular, and rotational changes to bring the spatial relationships within maximum values.

18. The imaging system of claim 1, wherein the spatial relationships comprise a relative distance, angle, and orientation of the imaging units, and wherein the program instructions further control the system to perform the correcting of the images of the first and second image streams in response to the determining that the spatial relationships are less than or equal to the one or more thresholds, wherein the correcting comprises one or more of the following:
   a) stabilizing the images to reduce blurring;
   b) correcting the spatial relationships by compensating differences in tilt and rotation of the first and second imaging units;
   c) removing specular reflections and/or visual artifacts from the images;
   d) normalizing the images for exposure, color, and/or contrast.

19. The imaging system of claim 1, wherein the maximum values comprise a maximum value for an angle of the first imaging unit relative to the second imaging unit wherein the maximum value for the angle is 45 degrees.

* * * * *